United States Patent [19]

Tron

[11] Patent Number: 5,039,856
[45] Date of Patent: Aug. 13, 1991

[54] PROCESS AND DEVICE FOR QUANTITATIVE RADIATION ABSORPTION MEASUREMENT

[75] Inventor: José Tron, St. Medard-en-Jalles, France

[73] Assignee: Societe Nationale Industrielle Aerospatiale, Paris, France

[21] Appl. No.: 817,415

[22] Filed: Jan. 9, 1986

[30] Foreign Application Priority Data

Jan. 16, 1985 [FR] France ................. 85 00600

[51] Int. Cl.$^5$ .............................................. G01N 23/02
[52] U.S. Cl. ................................ 290/358.1; 250/359.1
[58] Field of Search ................ 250/358.1, 359.1; 378/4, 19, 901, 51, 55, 54, 56; 364/414

[56] References Cited

U.S. PATENT DOCUMENTS

| | | | |
|---|---|---|---|
| 3,983,368 | 9/1976 | Csakvary et al. | 378/51 |
| 4,144,570 | 3/1979 | Wagner | 378/901 |
| 4,283,629 | 8/1981 | Habermehl | 378/4 |
| 4,393,305 | 7/1983 | Shimizu et al. | 250/358.1 |
| 4,511,801 | 4/1985 | Tatham et al. | 378/51 |

OTHER PUBLICATIONS

Greenleaf et al, "(Acoustic) Reconstruction of Spat. Dist. of Attenu. in Tissues ... )", NBS Special Pub. 453, p. 109 (1976).

*Primary Examiner*—Jack I. Berman
*Assistant Examiner*—Richard Hanig
*Attorney, Agent, or Firm*—Marshall, O'Toole, Gerstein, Murray & Bicknell

[57] ABSTRACT

A process and a device are provided for the quantitative radiation absorption measurement of a work piece using an electromagnetic radiation beam. In accordance with the invention, the work piece is scanned by sections and each section scanned is fictitiously divided into a plurality of zones, for each of which the value of the coefficient of attenuation per unit of length of said beam is determined.

4 Claims, 6 Drawing Sheets

PROCESS AND DEVICE FOR QUANTITATIVE RADIATION ABSORPTION MEASUREMENT

The present invention relates to a process and device for the quantitative measurement of radiation absorption.

BACKGROUND OF THE INVENTION

1. Field of the Invention

Although not exclusively, it applies particularly well to the contactless non destructive testing of the density and homogeneity of different parts made from composite or hybrid materials. By "composite materials" is designated hereafter a variety of materials generally of not very high density comprising a main phase called matrix and one or more phases of macroscopically or microscopically different natures, either chemically or physically (doped materials, fibrous materials), whereas the term "hybrid" relates to materials or structures comprising inserts made from isotropic materials, for example metal inserts.

2. Description of the Prior Art

For a long time it has been known to use ionizing radiation for determining, either thicknesses, or densities of different materials. More recently, and because of progress in optoelectronics and automation, systems using X rays and image reconstitution techniques have been put into practice in the medical field (x ray scanners, gamma camera), for making tomographies of the organs of the human body. However, the apparatus are not devices giving quantitative measurement.

In industry, these techniques have been developed almost exclusively in metallurgy for the final control of metal structures, (cracks, welds), or in forming laminates (regulation of the machines, thickness of the castings, etc. ...).

Up to the present time, there exists no system adapted to the requirements of the composite material industry.

SUMMARY OF THE INVENTION

The invention provides then an industrial high precision quantitative measurement device adapted to the analysis of density variations inside composite or "hybrid" materials, which materials are macroscopically heterogeneous, but whose quality depends on the homogeneous distribution of the heterogeneities.

The process and device of the invention allow then defects of homogeneity in tested work pieces to be sought, located and measured.

The industrial character of the invention is given by technological solutions for testing work pieces in a minimum of time The automatism of all the functions is therefore a determining factor of the system.

For rapid analysis of the results, the device allows the "out of tolerance" work pieces to be designated in accordance with criteria defined beforehand by the requirement specifications of the product to be tested. The machine gives then this type of information directly and in litigious cases (outer tolerance limits) allows the detailed analysis thereof to be made.

Preferably; the invention uses a gamma photon beam from suitably chosen radioactive sources. Of course, the device of the invention guarantees safety from radioactivity and complies perfectly with the standards in force in this field (ionizing radiation) without involving an individual protection for the operators.

The simple design, with respect to systems such as X ray scanners, makes it a device capable of quantitative measurements reducing the interpretation part to a strict minimum for there is no image reconstitution; consequently the cost of the device of the invention is substantially less than that of a scanner.

For this, in accordance with the invention, the process for the quantitative measurement of radioabsorption of a work piece using an electromagnetic radiation beam, in which a plurality of sections of said work piece are observed successively by means of said beam and the attenuation undergone by this latter is measured, is remarkable in that:

A—Each section observed is subdivided fictitiously into a first plurality of contiguous individual zones, with each of which is associated an unknown representing the attenuation per unit of length of said zone with respect to said beam;

B—Each of said sections is scanned with said electromagnetic radiation beam while communicating to this latter and to the zones of the corresponding section a second plurality of relative positions, which is chosen greater than said first plurality of individual zones;

C—Then, for each of these relative positions:
 a—the length of the path travelled by said beam in each of said zones through which it passes is calculated;
 b—an equation term S is formed, formed by the sum of the different products of the attenuation coefficient per unit of length multiplied by the length of the path of the beam, for each of the zones passed through by said beam;
 c—the intensity I of the beam is measured after having passed through the corresponding zones of the section and the expression $$\log \frac{Io}{I}$$

is formed, Io being the intensity of the beam before passing through said zones;
 d—the following equation is formed:

$$\log \frac{Io}{I} = S$$

D—After which, for all of said relative positions between said beam and said zones of the section, the different equations $$\log \frac{Io}{I} = S$$

are gathered together, so as to form a system of equations which is resolved for determining the value of the coefficient of attenuation per unit of length of each zone of the section.

Thus, it is then possible to compare the different attenuation coefficient values per unit of length obtained and to determine the possible zone or zones of the section having a defect of homogeneity.

Operating thus for a plurality of successive sections of said work piece, it is no longer the zones which are determined but volumes presenting defects of homogeneity.

To effect the different calculations, an electronic computing system is used. The diagram of the subdivision of each section into zones and the position of the electromagnetic radiation beam is communicated thereto. It is then capable of determining the zone through which the beam passes and the length of the path of said beam inside each zone. It then readily establishes the system of linear equations and may determine the desired values of the attenuation coefficients, zone by zone. Of course, this electronic computing system is advantageously used for controlling the relative movements between the zones of one section and said beam as well as for controlling the passage of said beam from one section to another.

In order to simplify the calculations, each section observed of said work piece is subdivided into individual zones having a square or rectangular shape and divided into lines and columns parallel to two rectangular directions and, in at least some of said relative positions between the beam and said zones, said beam is parallel to one or other of said directions. For at least some of said relative positions between the beam and said zones of a section, the beam may also be parallel to one or other of the diagonals of said square or rectangular zones.

For further simplifying the calculations, it is advantageous for the relative movements between the electromagnetic radiation beam and the zones of a section to be effected step by step and for said beam to pass through the center of the zone or zones scanned at each step.

Furthermore, for simplifying the construction of systems generating and receiving the electromagnetic radiation beam, it is advantageous for the relative movements between the beam and the work piece to be obtained by moving said work piece, the beam remaining fixed. Thus, the generating system and the receiving system are themselves fixed and remain perfectly aligned during the measurements. However, for examining work pieces of different sizes and/or the same work piece under different orientations, it may be advantageous for the generating system and the receiving system to be able to come together or move away from each other along said beam.

For putting the method of the invention into practice, an advantageous embodiment of the device comprises:

a rigid fixed chassis on which are mounted a system for generating electromagnetic radiations and a system receiving said radiations, said generating and receiving systems defining a fixed path for a beam of said electromagnetic radiations;

a base mounted movable in translation with respect to said rigid fixed chassis so as to be able to move step by step in a direction orthogonal to said fixed path of the beam, while remaining parallel thereto;

a table mounted on the base, so as to be able to move step by step in its plane which is orthogonal to the movement of said base; and a plate mounted for rotation on said table and capable of occupying several angular positions about its axis, which is orthogonal to the plane of said table, said plate being intended to support said work piece.

It is advantageous for said fixed path of the beam to be horizontal.

Moreover, preferably, the electronic computing system used for effecting the different calculations controls the different relative movements between said electromagnetic radiation beam and said work piece.

The electromagnetic radiation scanning beam is advantageously a gamma ray beam.

BRIEF DESCRIPTION OF THE DRAWINGS

The Figures of the accompanying drawings will better show how the invention may be put into practice.

In these Figures, identical references designate similar elements.

DESCRIPTION OF THE PREFERRED EMBODIMENTS

Figure 1:
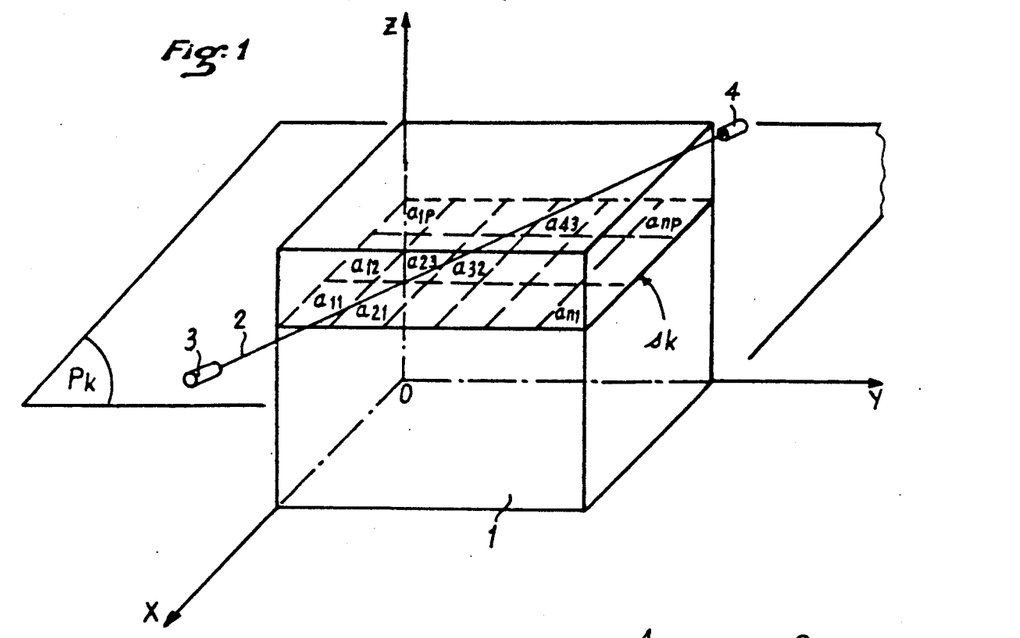
FIGS. 1 and 2 illustrate schematically the method of the invention.

In FIG. 1, a work piece 1 has been shown in perspective whose radiation absorption it is desired to measure quantitatively in accordance with the present invention. Intentionally, the work piece 1 has been shown with particularly simple shape (parallelepiped), so as to facilitate the drawings and the explanations. It is however obvious that the invention is not limited to this simple shape and applies whatever the shape of the work piece to be tested.

The work piece 1 is related to a system of orthogonal axes OX, OY, OZ, whose origin O merges with an apex of said work piece and said axes with the solid angles of intersection thereof. The work piece 1 is tested in a plurality of planes Pk, parallel to plane OX, OY and orthogonal to the axis OZ (with $k=1, 2, 3, \ldots q$).

Each plane Pk defines in work piece 1 a section sk which is observed by means of an electromagnetic radiation 2, for example a gamma ray beam, contained in the plane Pk. The beam 2 is delivered by a generating system 3 and received by a receiving system 4. The intensity of beam 2 at the output of the generating system 3 is assumed to be equal to Io; it is for example expressed as a number of gamma photons per second.

Figure 2:
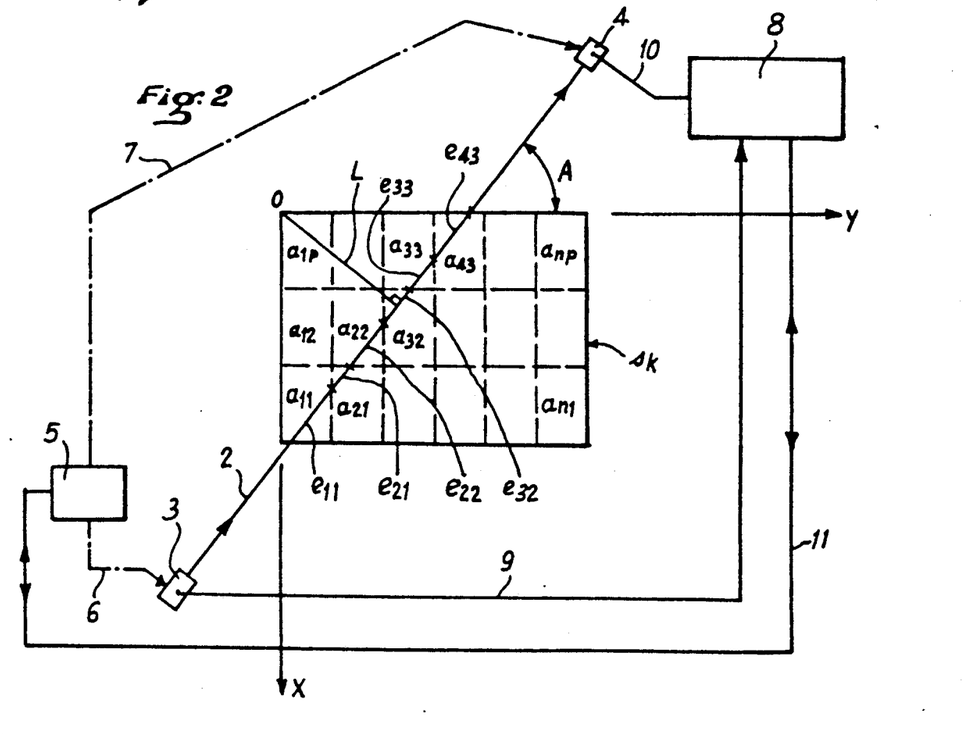

As shown in FIGS. 1 and 2, each section sk is fictitiously subdivided into a plurality n.p of individual square or rectangular zones aij (with $1 \leq i \leq n$ and $1 \leq j \leq p$), divided up into lines and columns parallel to the axes OX and OY. With each of said zones aij is associated an unknown xij representing the unit of length attenuation coefficient of said zone, with respect to beam 2.

Mechanical means 5 are provided (see FIG. 2) capable of simultaneously moving the generating 3 and receiving 4 systems (connections 6 and 7), while maintaining these latter aligned so that:

beam 2 may be brought into any desired plane Pk, orthogonal to the axis OZ, so that said beam may observe any desired section sk;

the beam 2 may scan each section sk, while occupying in the corresponding plane Pk, a plurality N of different relative positions with respect to said zones aij (with $N > n.p$). These different relative positions may be obtained by the fact that said mechanical means 5 cause the slope A of beam 2 to vary with respect to the axis OY about the axis OZ and/or the distance L from the beam 2 to said axis OZ.

In a section sk, for each relative position between the beam 2 and the zones aij, with the thickness of the work piece 1 through which beam 2 passes known:

a) the length eij of the path of the beam is calculated in each of said zones aij through which it passes. For this, an electronic computing system 8 is provided which knows the position of the generating 3 and receiving 4 systems (connections 9 and 10) and so the slope angle A and the distance L. In addition, the electronic computing system 8 knows the subdivision of section sk into zones aij; it is therefore capable of calculating the different lengths eij of the path of the beam 2 in the areas aij.

In the example shown in FIG. 2, beam 2 passes through the zones a11, a21, a22, a32, a33 and a43. Subsequently, the electronic computing system 8 which knows this situation through connections 9 and 10 calculates the path-length e11, e21, e22, e32, e33, and e43.

b) an equation term S is formed, comprising the sum of the different products of the attenuation coefficient per unit of length xij multiplied by the length eij of the path of beam 2, for each of the areas aij passed through by said beam.

Generally, $S = \Sigma xij \cdot eij$

In the example shown in FIG. 2;

$S = x11.e11 + x21.e21 + x22.e22 + x32.e32 + x33.e33 + x43.e43$

Of course, the term S is formed by the electronic computing system 8.

c) using the receiver system 4, the intensity I of beam 2 is measured after passing through corresponding zones iaj of section sk and the value I is fed to the computing system 8 (connection 10). This latter then calculates the expression $$\text{Log} \frac{Io}{I}$$

and forms the equation $$\text{Log} \frac{Io}{I} = \Sigma xij \cdot eij.$$

Thus, for each of the relative positions between beam 2 and zones aij resulting from the action of the mechanical means 5, such an equation is obtained. Subsequently, if the N equations determined by the N relative positions of beam 2 and zones aij are gathered together, an equation system is obtained for determining (by means of the computing system 8) each of the unknown values xij.

By comparing these values xij the possible zones aij may be determined corresponding to an abnormal value xij, so to a heterogeneity. It will be noted that the density dij of the material of the zone aij is equal to:

$$dij = \frac{sij}{K},$$

K being the attenuation coefficient per unit of mass.

This attenuation coefficient per unit of mass K only depends on the energy of the gamma photons of beam 2 and on the elementary nature of the material of work piece 1. Consequently, the computing system 8 may readily calculate the densities dij.

A connection 11 is provided between the computing system 8 and the mechanical moving means 5 for controlling the passage of beam 2 from one plane Pk to another and the scanning of each of the sections sk.

Figure 3:
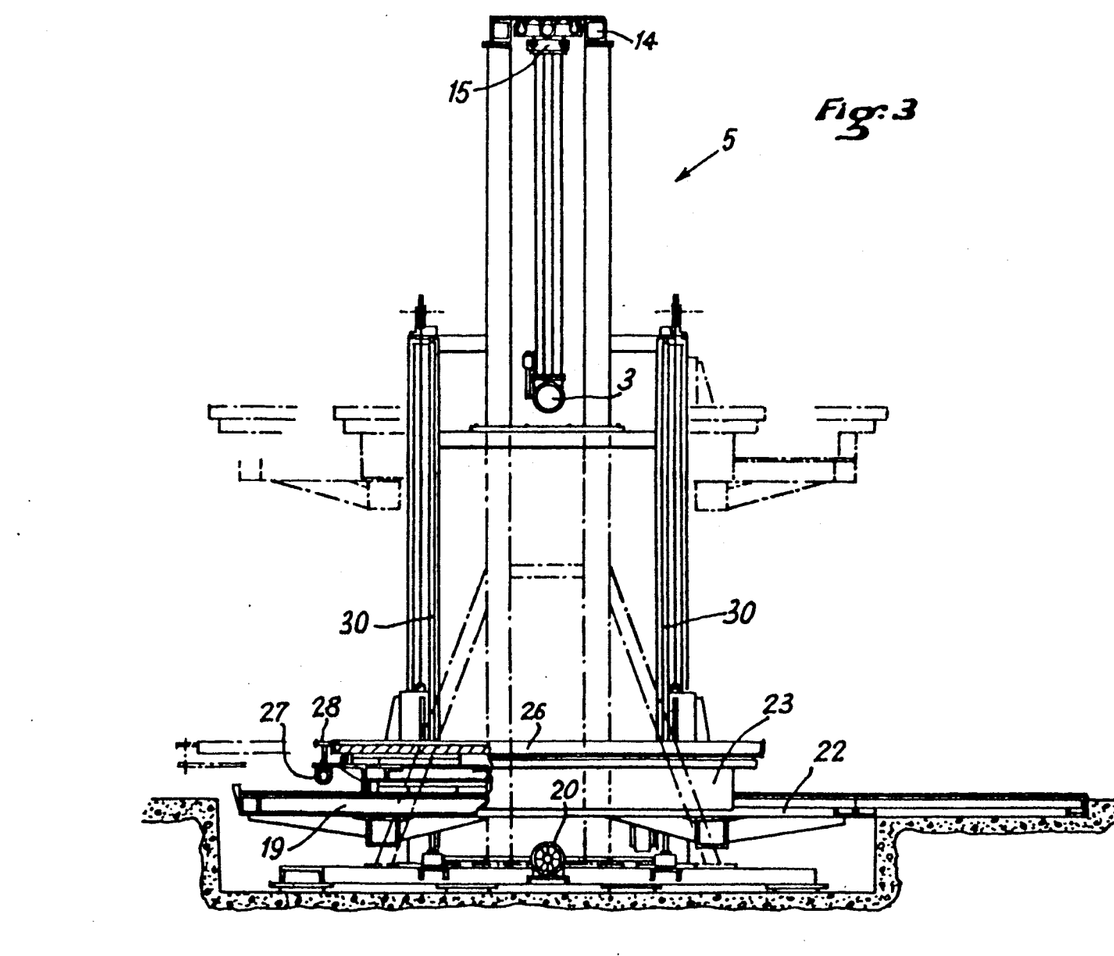
FIG. 3 is an elevational view of the machine for implementing the method of the invention.
Figure 4:
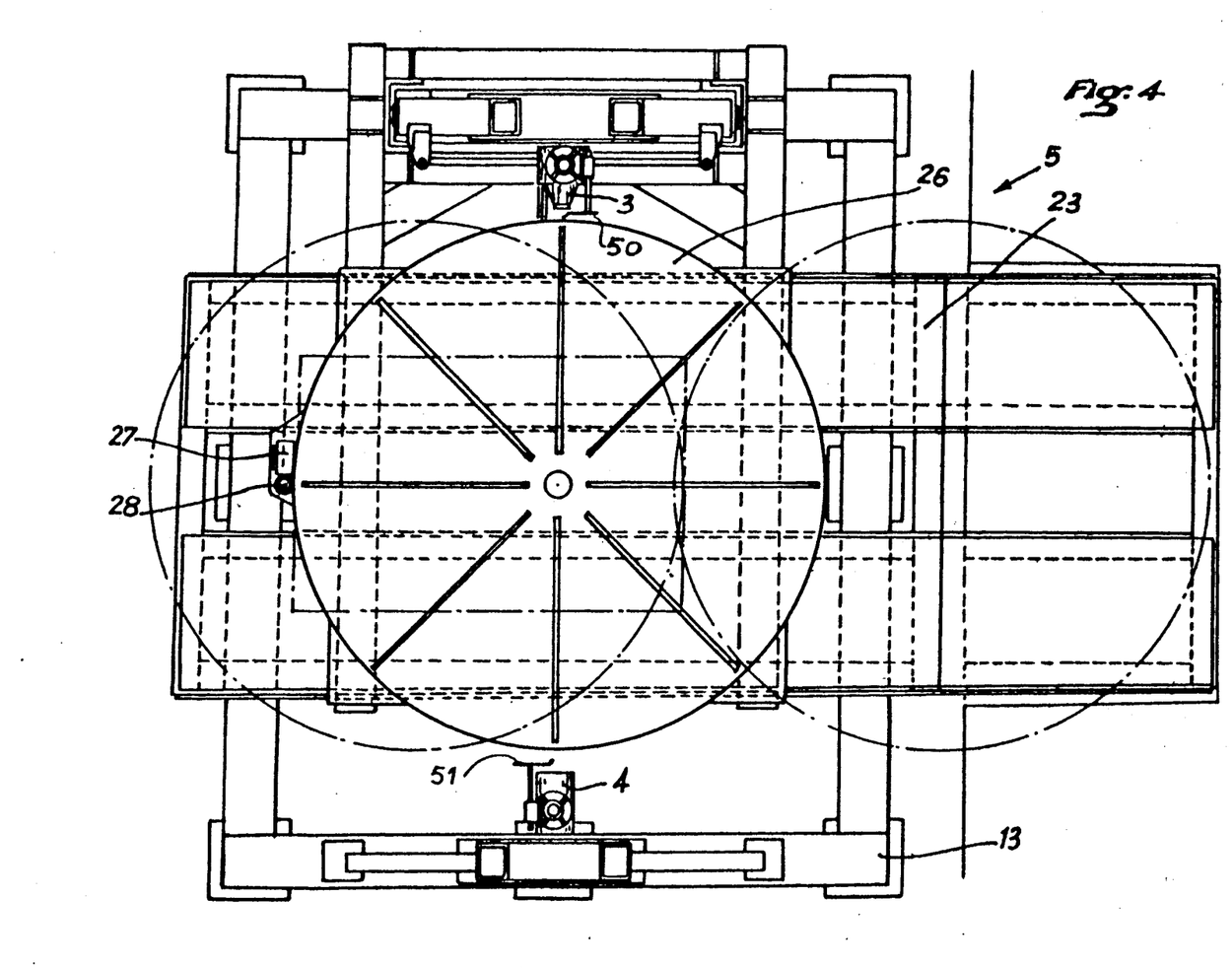
FIGS. 4 and 5 are respectively top and side views of the machine of FIG. 3, FIGS. 6 to 11 illustrate the operation of the machine of FIGS. 3 to 5.
Figure 5:
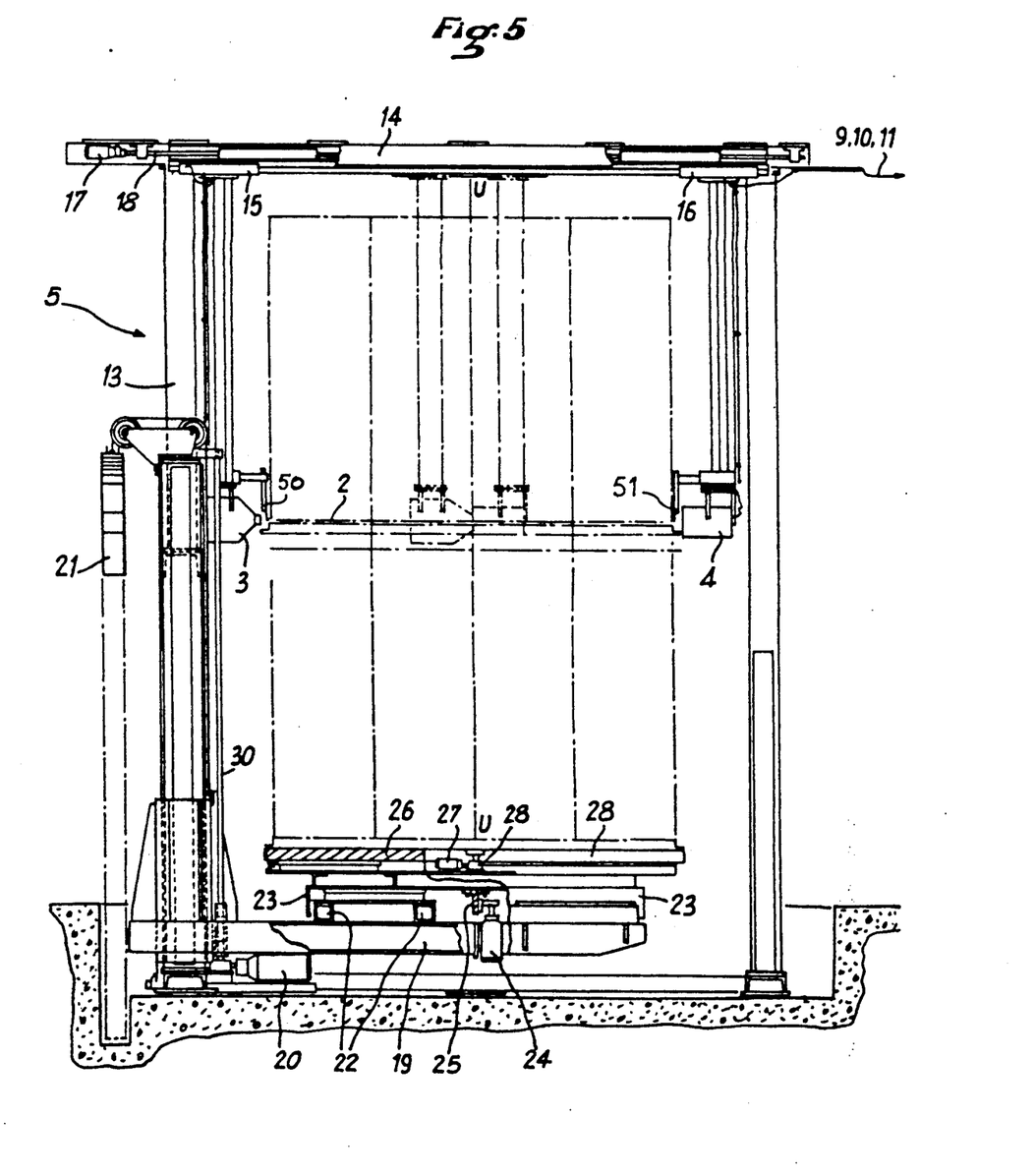

In FIGS. 3, 4 and 5 has been shown one embodiment of the mechanical moving means 5. They comprise a gantry 13 having a horizontal beam 14. On said beam 14 are slidably mounted coupled carriages 15 and 16 which may be drawn together or moved apart from each other symmetrically with respect to the median vertical axis U—U of gantry 13. The radiation generating system 3 is suspended from carriage 15, whereas the receiving system 4 is suspended from carriage 16. Thus, the systems 3 and 4 are movable symmetrically with respect to each other under the action of motor 17 and the endless screw 18 driving carriages 15 and 16.

In a variant, said carriages 15, 16 may also support a device for measuring the thicknesses of piece 1 through which beam 2 passes successively. Said measuring device then comprises feelers 50, 51 for transmitting the data to the computing device 8.

The mechanical means 5 further comprise a horizontal base 19 capable of moving in vertical translation along uprights of the gantry 13, under the action of a motor 20 and an endless screw 30. Counterweights 21 are provided for facilitating the vertical movements of the horizontal base 19.

On the horizontal base 19 are provided horizontal rails 22 over which a horizontal table 23 may slide under the action of a motor 24 and a rack 25.

In addition, on the horizontal table 23 is mounted plate 26 rotatable about a vertical axis under the action of a motor 27 and a pinion drive 28.

Operation of means 5 of FIGS. 3 to 5 is illustrated in FIGS. 6 to 11.

Figure 6:
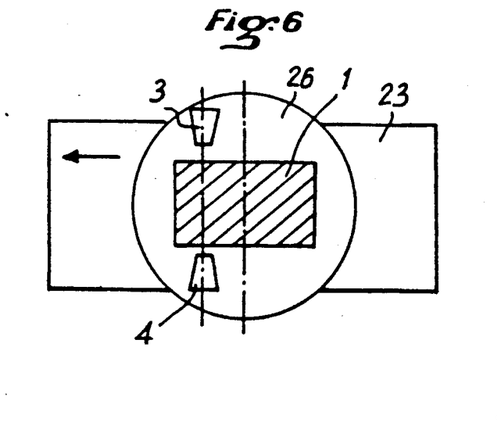
Figure 7:
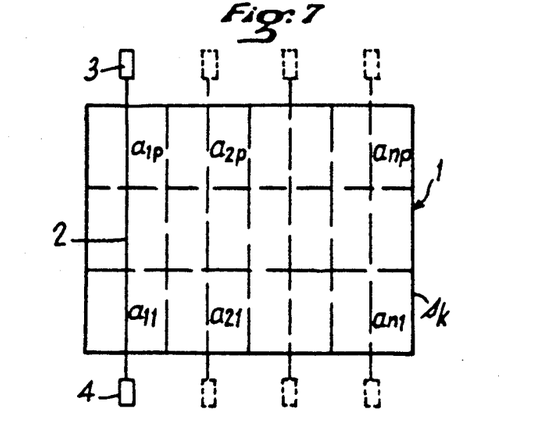

With work piece 1 loaded on plate 26, motor 20 is actuated for moving the base 19 vertically so that the generator system 3 and the receiver system 4 are at the level of the horizontal section sk of work piece 1 to be observed. Then, motor 20 is stopped and motor 24 is actuated. Table 23 and plate 26 then move horizontally, step by step, between source 3 and detector 4 (FIG. 6). At the first step, the beam 2 passes simultaneously and centrally through p zones a11, a12, ... a1p of section sk (FIG. 7). At the second step, it is zones a21, a22, ..., a2p which have the beam passing centrally therethrough, etc. ... At the nth step, the beam 2 passes centrally through the zones an1, an2, ..., anp.

Figure 8:
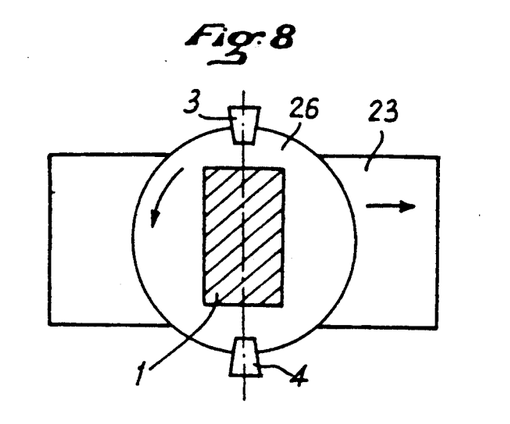
Figure 9:
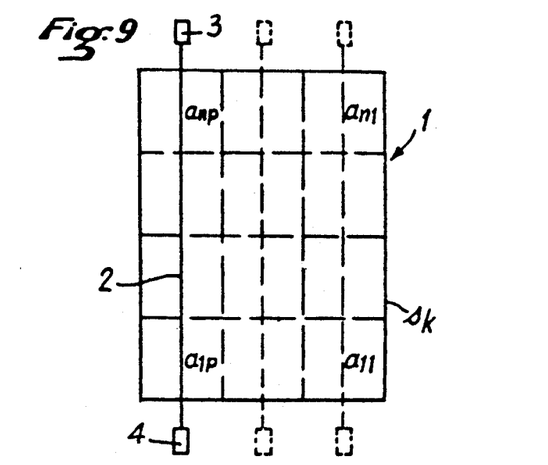

After this nth step, motor 27 is actuated and plate 26 rotates by a quarter of a revolution. Then, motor 24 is actuated in the reverse direction to the preceding one (FIG. 8). Table 23 and plate 26 then travel horizontally again between source 3 and detector 4, but in the opposite direction. At the first step, beam 2 may pass centrally and simultaneously through the zones a1p to anp, then at the second step zones a1(p−1) to an(p−1), etc. ... At the pth step, the beam 2 passes centrally through the zones a11 to an1 (FIG. 9).

Figure 10:
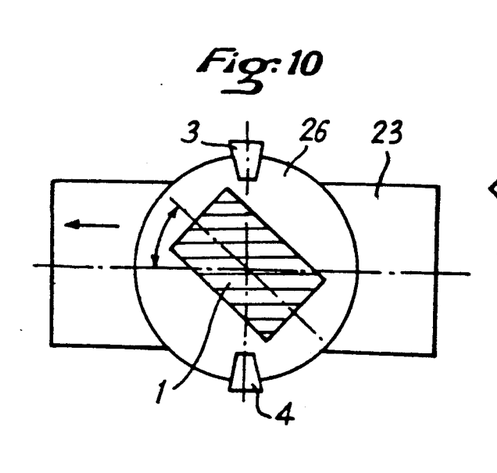
Figure 11:
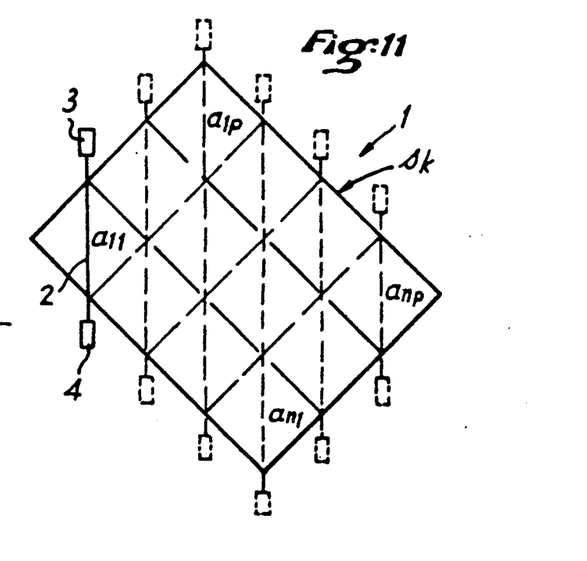
Figure 12:
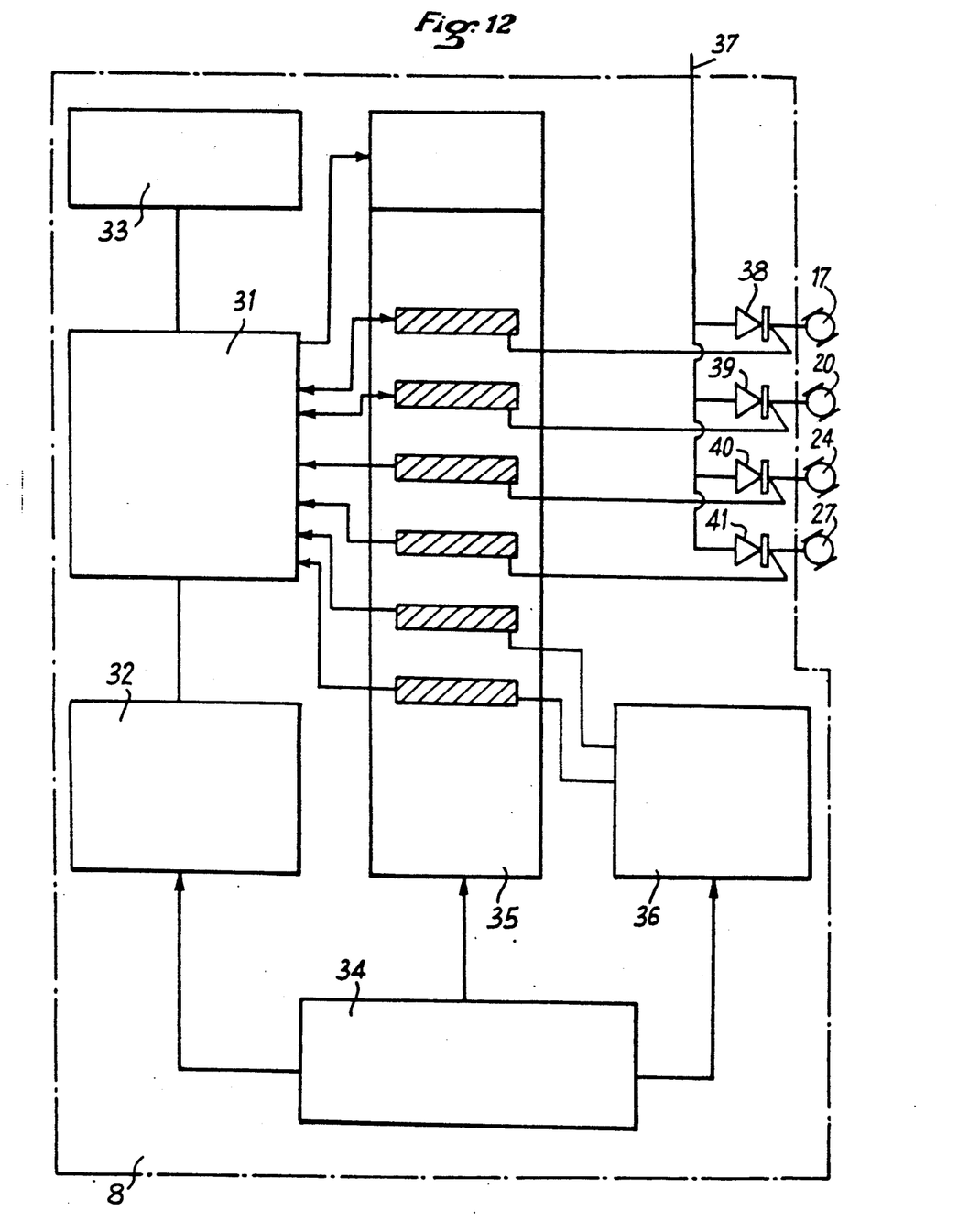
FIG. 12 gives the block diagram of an electronic computing system for controlling the machine of FIGS. 3 to 5.

Then, the motor 27 is actuated for rotating the work piece 1 by an eighth of a revolution (FIG. 10). By causing the work piece 1 to travel again between source 3 and detector 4, it is then possible to scan the different zones aij diagonally (FIG. 11). In this case, motor 17 is actuated so that, at each step, the distance (along the beam 2) between the generating system 3 and the receiving system 4 to the work piece 1 is constant and equal to what it was during the tests of FIGS. 6 to 9.

The embodiment of the electronic computing system 8, shown in FIG. 6, comprises a processor 31 associated with a keyboard console 32 and with a display device 33, a control desk 34, a memory block arrangement 35, a measuring chain 36 and controlled switches 38 to 41, adapted for controlling the power supply to the different motors 17, 20, 34 and 27 from a power line 37.

The arrangement 35, for example of the VME type (versa-module-european) of the firm MOTOROLA forms the essential member of the system. It comprises an assembly capable of receiving a certain number of modules adapted for providing particular functions independently:

movement control function, a function for managing the measuring chain 36, connection between the processor 31 and the measuring chain 36, memory support.

Processor 31 provides mainly the following functions:

processing of measurements—statistics and corrections, construction of the matrix of the elementary path lengths of the beam in the zones from geometrical data concerning said zones.

The measuring chain 36 processes the signals delivered by the detector system 4 formed, for example, by a scintillator-photomultiplier-charge preamplifier.

The parameters required for carrying out the sequence and for calculating the thicknesses passed through (meshing) are entered on console 32.

The display device 33 may be used among other things for representing the beam 2 and the section of the object through the horizontal plane containing the beam as well as the meshing.

The sequential operation of the system may be as follows:

0) Preliminary adjustments the generator 3—detector 4 distance is adjusted;

loading of the work piece 1 to be analysed;

loading of the source of the generating system 3.

1) Preliminary measurements when the work piece 1 is fixed on its support 26 and disposed outside beam 2, the active memories of the arrangement 35 are reset by means of the console keyboard 32.

the counting time is displayed on the console for measuring the intensity of the beam Io. The discrimination threshold (spectrum displayed on the multichannel analyser) of the measuring chain 36 is adjusted.

the counting time is displayed on the console for measuring the background noise (collimater of the obturated generator 3).

the results are stored in the processor.

2) Sequential measurements

The sequence depends on the nature and on the geometry of work piece 1. A certain independence may be attributed to each module of arrangement 35 so that a function corresponds to a module. It is then sufficient to initialize the different parameters.

positioning in space duration of the counts number of steps and to display the sequential logic.

Counting is initiated by a logic signal delivered at the time when work piece 1 is positioned, the thickness measurement being effected.

As soon as counting is finished, a logic signals is delivered and the sequence continues.

Processor 32 receives through arrangement 35 the geometrical data corresponding to the measurement carried out and the values of the count.

In masked time it processes the measurements (statistics and corrections) and computes the thicknesses through which the beam passes in each zone of the meshing, the geometrical parameters of the meshing having been introduced by the console keyboard and stored in the processor.

The results are fed to a memory of arrangement 35 and introduced with a time lag into computer 31 for calculating the relative or absolute densities of each of the zones of the meshing. The computer is programmed for designating the work pieces "within" or "outside" tolerances.

The electromagnetic radiation generating system 3 may comprise:

a sealed radioactive source (elimination of the contamination risks) whose nature and activity depend on the structure of the work pieces to be analyzed. It responds to the requirements of accuracy because of the faculty of changing:

the nature and activity of the source, the duration and number of measurements.

This source is for example cobalt 60.

screening of the source providing an exposure level lower than that defined by the radioactivity protection standards in force.

a collimater for obtaining a gamma beam of small opening, whose geometry is adapted to the nature of the structure.

The receiving system 4 may comprise:

a high time resolution and high efficiency gamma photon detector (scintillator—semiconductor).

a high speed amplifier and discriminator.

and a high speed counting scale.

The present invention is particularly well adapted for use in the industry of new materials (composite materials: solid textile materials, spooled materials, multidirectional materials, comprising fibers in more than two directions, random orientated materials, charged or doped materials . . . ) for which knowledge of the density homogeneity of the structure is an essential quality factor.

The availability of the measuring device of the invention is an important advantage for the non destructive testing of said quality.

Of course, the device of the invention is adaptable to metal structures as well as for "hybrid" materials.

What is claimed is:

1. A quantitative radiation absorption measurement device comprising:

a fixed rigid chassis, on which are mounted an electromagnetic radiation generator and a system receiving said radiation, said generator and receiving system defining a fixed path for an electromagnetic radiation beam, a base mounted movable in translation with respect to said fixed rigid chassis so as to be able to move step by step in a direction orthogonal to said fixed path of the beam while remaining parallel thereto;

a table mounted on said base so as to be able to move step by step in its plane which is orthogonal to the movement of said base; and a plate mounted for rotation on said table and able to occupy several angular positions about its axis, which is orthogonal to the plane of said table, said plate being intended to support a work piece.

2. The quantitative radiation absorption measurement device as claimed in claim 1, wherein said path of the beam is horizontal.

3. The quantitative radiation absorption measurement device as claimed in claim 1 or 2, wherein the distance between the electromagnetic radiation generator and the receiving system is adjustable along said beam.

4. The quantitative radiation absorption measurement device as claimed in claim 1 to 3, comprising an electric computing system carrying out the different calculations and controlling the movement of the base, of the table and of the plate.

* * * * *